(12) United States Patent
Harrington et al.

(10) Patent No.: US 9,486,235 B2
(45) Date of Patent: Nov. 8, 2016

(54) SURGICAL DEVICE EMPLOYING A CANTILEVERED BEAM DISSECTOR

(71) Applicant: Michael Rontal, Farmington Hills, MI (US)

(72) Inventors: Rick Harrington, Dexter, MI (US); Charles W. Krapf, Livonia, MI (US); Michael Rontal, Farmington Hills, MI (US); Ryan Klock, Ann Arbor, MI (US)

(73) Assignee: Michael Rontal, Bloomfield Hills, MI (US)

( * ) Notice: Subject to any disclaimer, the term of this patent is extended or adjusted under 35 U.S.C. 154(b) by 0 days.

(21) Appl. No.: 14/641,791

(22) Filed: Mar. 9, 2015

(65) Prior Publication Data

US 2015/0257778 A1    Sep. 17, 2015

Related U.S. Application Data

(60) Provisional application No. 62/039,783, filed on Aug. 20, 2014, provisional application No. 61/950,924, filed on Mar. 11, 2014.

(51) Int. Cl.
| | |
|---|---|
| *A61B 17/32* | (2006.01) |
| *A61B 17/22* | (2006.01) |
| *A61B 17/24* | (2006.01) |
| *A61B 17/00* | (2006.01) |

(52) U.S. Cl.
CPC ... *A61B 17/320068* (2013.01); *A61B 17/2202* (2013.01); *A61B 17/22012* (2013.01); *A61B 17/24* (2013.01); *A61B 2017/00734* (2013.01); *A61B 2017/320072* (2013.01); *A61B 2017/320096* (2013.01)

(58) Field of Classification Search
CPC ................. A61B 17/320068; A61M 25/0158; B06B 1/0603
USPC ......................................................... 606/169
See application file for complete search history.

(56) References Cited

U.S. PATENT DOCUMENTS

| | | | | |
|---|---|---|---|---|
| 5,154,694 A | * | 10/1992 | Kelman | A61F 9/00745 604/22 |
| 5,188,111 A | * | 2/1993 | Yates | A61B 1/0058 128/DIG. 7 |
| 5,197,946 A | * | 3/1993 | Tachibana | A61M 5/00 604/22 |
| 5,281,213 A | * | 1/1994 | Milder | A61B 18/02 606/15 |
| 5,397,340 A | * | 3/1995 | Nyman | A61M 25/0116 604/95.01 |
| 5,415,633 A | * | 5/1995 | Lazarus | A61M 25/0158 600/434 |
| 5,728,089 A | * | 3/1998 | Lal | A61B 17/320068 601/2 |
| 5,931,805 A | * | 8/1999 | Brisken | A61B 17/22012 604/22 |
| 6,087,863 A | * | 7/2000 | Aflatouni | H05B 33/08 327/111 |
| 6,272,371 B1 | * | 8/2001 | Shlomo | A61B 5/06 128/899 |
| 6,629,341 B2 | * | 10/2003 | Wilkie | H01L 41/082 156/222 |
| 8,137,371 B2 | * | 3/2012 | Cuny | A61B 17/320068 606/169 |
| 8,945,113 B2 | * | 2/2015 | Brannan | A61B 18/00 606/34 |

(Continued)

*Primary Examiner* — Julie A Szpira
(74) *Attorney, Agent, or Firm* — Dinsmore & Shohl LLP

(57) ABSTRACT

A surgical instrument for treating body tissues through narrow body passages employs an elongated cantilevered beam having a proximal end supported in a rigid block and a narrower distal end extendable through the narrow passages. One or more piezoelectric actuators are fixed to the beam surface and energized from an AC source through electrodes interspersed with the piezoelectric actuators to produce oscillatory motion of the beam distal end in multiple modes of movement with sensing electronics to monitor and control the distal mechanical movement.

18 Claims, 11 Drawing Sheets

(56) References Cited

U.S. PATENT DOCUMENTS

2002/0052617 A1* 5/2002 Anis ................... A61F 9/00763
606/169
2007/0114890 A1* 5/2007 Churchill ............ H01L 41/1136
310/339
2007/0123809 A1* 5/2007 Weiss ..................... A61H 21/00
601/84
2008/0272672 A1* 11/2008 Higashionji ........... H02N 2/004
310/317
2010/0118405 A1* 5/2010 Allison ................. G02B 6/022
359/579

* cited by examiner

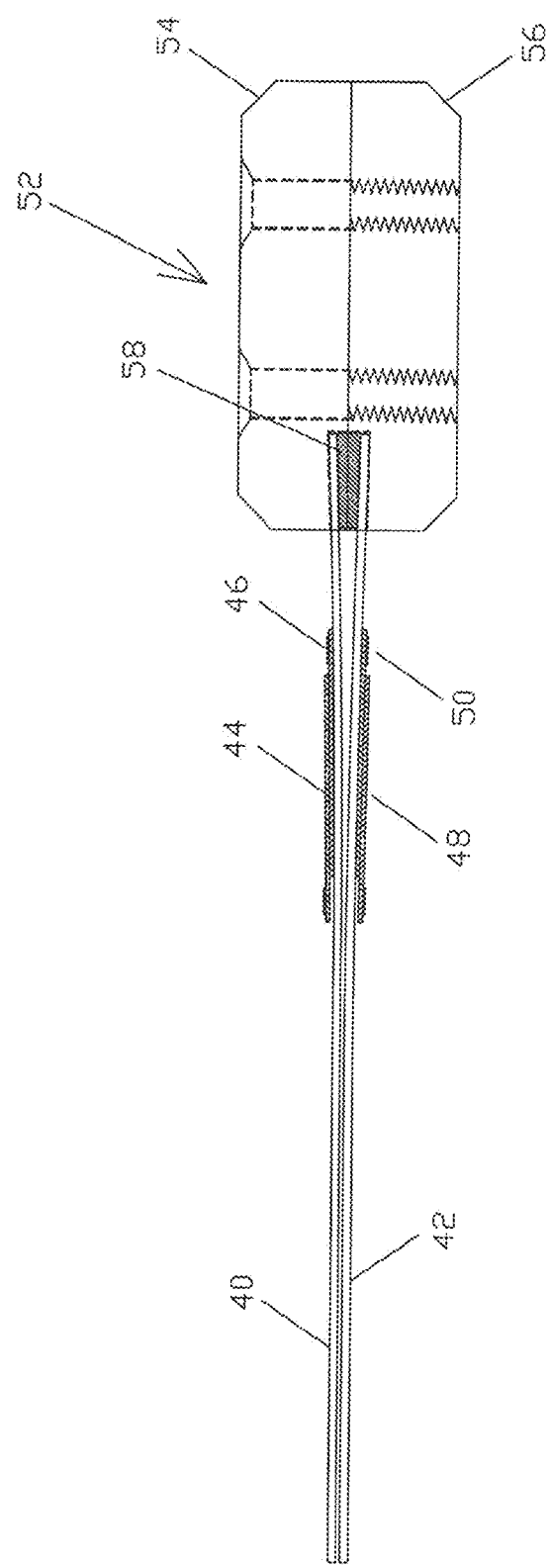

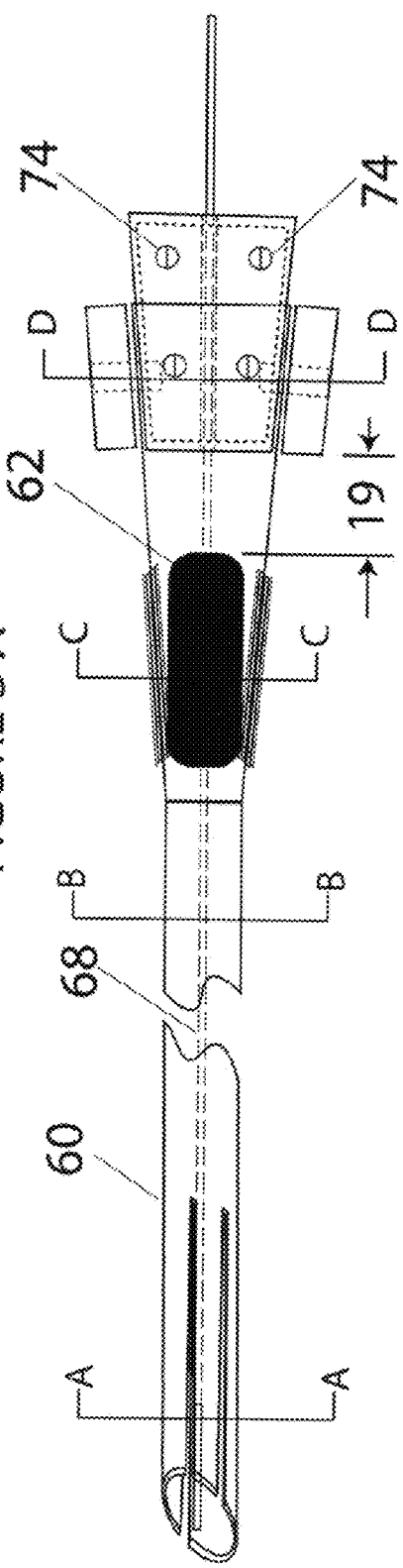
FIGURE 5A
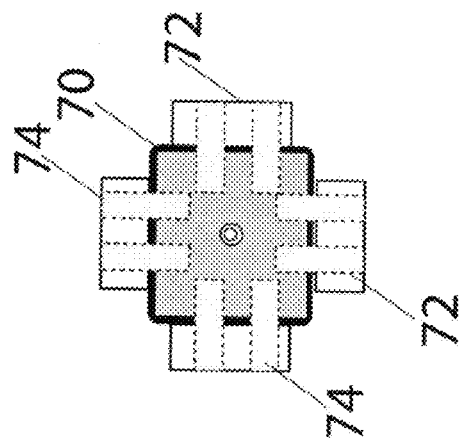
FIGURE 5E
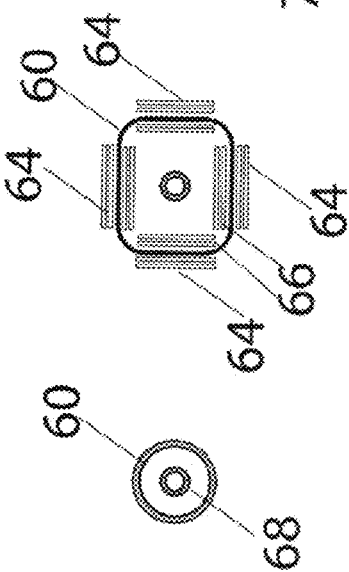
FIGURE 5D
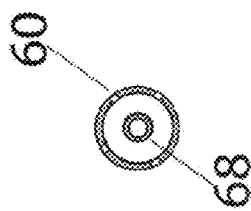
FIGURE 5C
FIGURE 5B

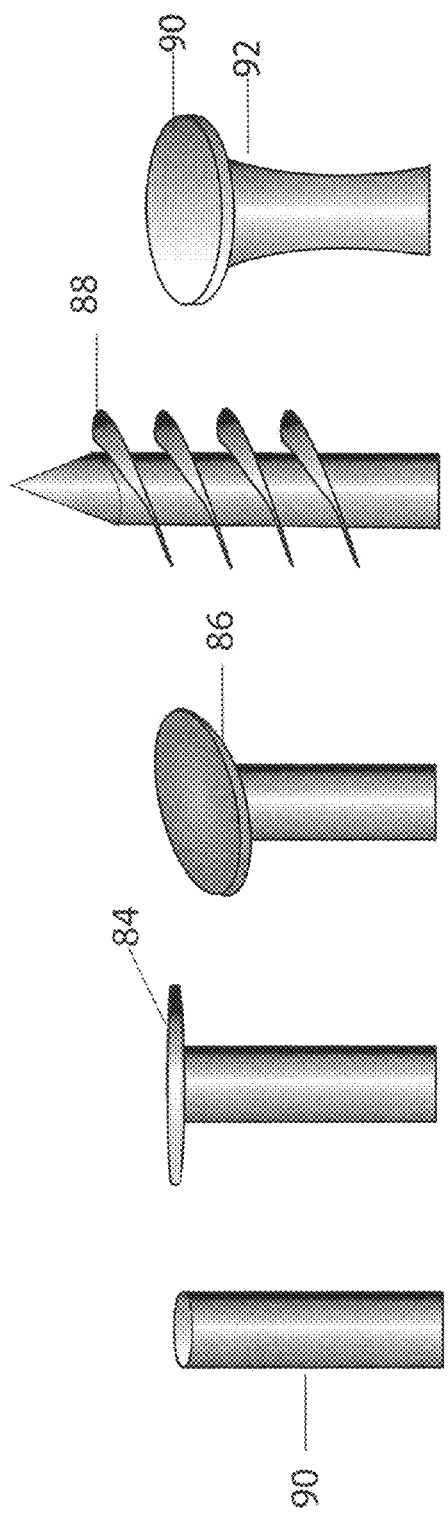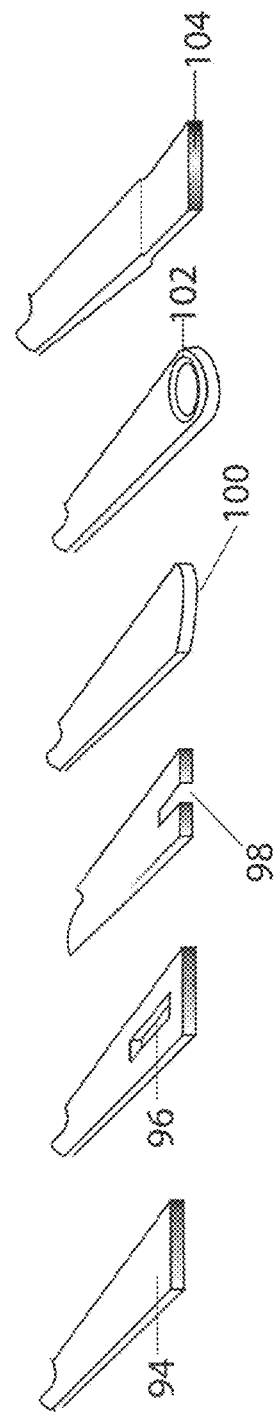

SURGICAL DEVICE EMPLOYING A CANTILEVERED BEAM DISSECTOR

CROSS-REFERENCE TO RELATED APPLICATIONS

This application claims priority of U.S. Provisional Application No. 61/950,924 filed Mar. 11, 2014, and U.S. Provisional Application No. 62/039,783 filed Aug. 20, 2014, the contents of which are incorporated herein by reference.

FIELD OF THE INVENTION

This invention relates to surgical instruments comprising cantilevered beams driven by macro fiber composites (MFCs) to destroy, dissect, incise, coagulate, and/or otherwise treat tissues through openings and passages to targets within a mammalian body.

BACKGROUND OF THE INVENTION

Energy driven surgical tools which apply acoustic energy to tissues can cause tissue effects deep in the body structures through relatively long, narrow passages. For deep and narrow surgery many devices and techniques have been developed and used. For example, cold knife techniques using knife blades or a rotating suction debrider such as marketed by Medtronics have been employed. The latter is an improvement as it removes tissue and resulting blood. As procedures are usually done with an endoscope any bleeding rapidly obscures any visualization of the surgical site. To surgically manipulate tissue (disintegrate, incise, elevate and dissect) and not obscure the surgical field with blood, instruments which apply various forms of energy have been developed. These energies include heat, cold (cryosurgery), radio frequency, laser light, plasma and sound. Each of these by itself has advantages and faults. In this patent we present a device that purposely combines sound energy with cold steel technique.

The earliest realization of sound's effects on solid structures dates back to the early 1900s when it was discovered that when a boat propeller was rotated at a high speed the resulting cavitation could destroy the propeller. The effect was to cause or use small vapor bubbles within a liquid. A spinning propeller or sound energy as a repetitive production of powerful positive and negative movement in a liquid stores this energy in the walls of these vapor bubbles. The life of these high energy bubbles is very short and the stored energy is released quickly as the bubble collapses. In appropriate surgical instruments the energy of the bubble collapse is dissipated in four different forms: as a concussion wave that can break down tissue, through heat that is intense for a very short time and can cause chemical reactions not otherwise possible, as micro streaming of movement on the bubble outer surface capable of cleaning a nearby surface, and as a vortex that can drill into tissue cells, known as sonoporation.

Ultrasonic devices on the market today produce enough energy to cause a controlled tissue disintegration. The ultrasound is created proximally, concentrated into a waveguide, and conducted to a distal tip where cavitation is created. As the cavitation is the only working energy in this tool, very large ultrasonic generators are needed. Usually this is done with stacks of piezoelectric ceramic discs or a magnetostrictive system. A typical piezo actuator is constructed as described by Langevin. A stack of piezo ceramic discs are squeezed tightly between a blocking mass and a condenser using a bolt. As sound energy is created it travels in both a proximal and distal direction. The blocking mass prevents the spread proximally. The energy is thus all concentrated into the condenser which narrows on its distal end. A waveguide is attached to the condenser to then carry the sonic energy to the target. As the objective is to cause resonance in the waveguide trying to condense the energy at an antinode the length of the waveguide is dependent on the frequency of the sound. To achieve high energy levels at the distal end a thick, straight and rigid waveguide is created. The material transmits sound at a relatively high speed (for example using a titanium alloy with speeds of about 6100 m/s). The goal is to achieve resonance of the waveguide and produce an antinode at the distal tip. To do this a large amount of electrical energy is required. Once the tip of the resonating waveguide is placed in contact with tissues, the sound energy enters the water based tissue and creates cavitation. The cavitation destroys or otherwise is used for surgical purposes.

The cavitation occurs as a spherical cloud around the tip of the instrument. A smaller instrument has a smaller cloud and is thus both more precise and restricted in the speed of action. Such a device is used for cataract surgery, a very precise surgery.

The CUSA (cavitron ultrasonic surgical aspirator) is used in brain surgery. A larger energy source and waveguide associated with a suction tube is used for neurosurgical removal of brain tumors. Its advantage is the destructive cavitational effect on high water content tissue like brain tumors with little effect on relatively drier tissue like normal brain tissue, collagen and blood vessel walls. The cavitation produced disintegrates the tumor and an integrated suction removes the detritus. The difference in water content results in surgical precision at lower powers.

Another surgical tool that uses ultrasound is a harmonic scalpel. A rapid longitudinal, reciprocating movement imparted into a scalpel shaped blade results in cutting of tissue. The associated heat generated causes coagulation. The cutting is very precise due to the high rate of movement and the narrow loss of cells in the kerf.

Other surgical instruments employ tissue welding and coagulation produced by sound energy reduced to heat as a waveguide transmits sonic energy to tissues. Blood vessels can be fused closed or various clips can be fused to clamp vessels.

In the early 1990s trials of the CUSA for intranasal surgery (polypectomy) were conducted. This tool was excellent at removing tissue almost bloodlessly but was exceedingly slow. Trial use of CUSA for tonsillectomy has also been published. The advantages were precise extracapsular excisions with little bleeding.

The SonoPet was introduced recently for otolaryngology work. It is also a rigid straight hollow waveguide that suctions blood and detritus. It also is marketed with a variety of rasp tips for vibratory motion and bone abrading. From a nasal surgery standpoint, it is very good for abrading through bone into the frontal sinus and between the nose and braincase, with its greatest advantage being the slow precision in dangerous areas.

A device developed in Russia and found in eastern European clinics called a Tonsillor is another high-energy ultrasonic device. It is very powerful as it too works primarily through cavitation. It is proximately bulky and has a long, relatively thick, rigid waveguide with a variety of tips. It is used near the external surface and straight into the nasal passage as it is too large for precise intranasal work deep in the nose.

Other devices have been proposed that add ultrasound to a rotating suction knife device (debrider, Hummer, and the like).

SUMMARY OF THE INVENTION

It is the purpose of the present invention to provide surgical instruments that allow surgery in deep recesses through narrow passages such as the nasal passages and associated paranasal sinuses. For the purposes of this patent we will often cite surgery of the nose and paranasal sinuses. Those familiar with the art will understand that this device and method of surgical technique can be applied elsewhere. This device uses a narrow beam as a waveguide that is thin, at times curved with a small proximal end energy transducer. It works using both ultrasound and vibratory action so that it provides the advantages of cavitation plus tissue destruction with hemostasis of small vessels but can also provide a whipping/vibratory action at the beam tip. It is self-correcting for tissue effects on the beam and also can monitor the tissue viscosity for the surgeon to alert encountering bone or passing through tissue into air-containing spaces. This is all made possible by small flat transducers (macro fiber composite pads (MFCs)) and electronics that allow a mixing of ultrasound and acoustic vibration to do work at the distal end. The electrical source is direct current battery power.

The devices of the present invention for surgical tissue resection are quite different from previous ultrasound tools.

First, the thick, rigid, rod-like waveguides of modern ultrasound tools are substituted with a flat beam of stainless steel or some other rigid material. Second, the ultrasonic energy transducer is a Macro Fiber Composite (MFC). An MFC is a piezoelectric device which consists of layers of electrical insulator, interdigitated positive and negative electrodes, piezoelectric ceramic fiber, interdigitated positive and negative electrodes, and electrical insulator in that order, bonded together with a polymer or resin matrix into a patch form-factor. An electric field applied by the embedded electrodes poles (aligns on a molecular level) the crystals of the piezoelectric ceramic fibers to effect a mechanical elongation or contraction of the fibers. One or more MFCs are bonded to a widened proximal end of the aforementioned flat beam and conduct their mechanical energy down the length of the beam toward a tapered distal end as sonic and ultrasonic waves. To provide adequate mechanical force to distort the flat beam, multiple MFCs may be aligned or layered upon one another and electrically actuated in unison. Thirdly, the flat beam is cantilevered from a relatively massive blocking mass made of a highly rigid and dense material. This blocking mass serves to reflect stray sonic and ultrasonic waves toward the distal end of the flat beam. Fourthly, by controlling the phase of actuation of MFCs on either side of the flat beam, two modes of motion may be generated. An extensional motion (Fz mode) may be generated by actuating MFCs on either side of the flat beam in unison (0 degree phase shift). This Fz mode is characterized by a high-frequency, low displacement motion of the distal tip capable of inducing fluidic cavitation of animal tissues in contact with the distal tip of the beam. Alternatively, a transverse motion (My mode) may be generated by actuating MFCs on either side of the flat beam in an opposing fashion (180 degree phase shift). This My mode is characterized by a low-frequency, large-displacement whipping motion of the distal tip capable of minute tearing of animal tissue. Rapid transition between the Fz and My modes results in excellent tissue destruction and local hemostasis at the distal tip of the flat beam with precision control.

The output of the generator is wired to the MFCs and controlled by an H-bridge circuit that allows for very rapid switching between modes of MFC energization where MFC movement is mutually reinforcing, causing axial movement and at other times causing a bending movement of the beam tip. The result is movement of the tip in two planes to do the work of tissue removal. The MFCs can respond to rapid changes in excitation and this device makes use of two motions in the beam—a movement along the longitudinal axis of the beam (the Fz mode) and a movement in which the MFC on one side of the beam is expanding while the MFC on the other side is contracting (the My mode)—to cause the beam tip to move transverse to the beam plane. The My mode motion can be adjusted to a high frequency which essentially causes tearing and/or churning of the tissue, and the Fz motion can be turned on and off so rapidly as to appear simultaneous and thus cause tissue destruction by both tearing and cavitation. The cavitation also aids in initiating coagulation. The most deflection in the My mode is at the resonate frequency, however harmonics of the My resonate frequency will also cause significant distal end movement.

The duration for each mode and any delay between switching of modes is entirely controllable. This rapid interplay of these two movements results in excellent tissue destruction under precise control.

As the device uses both an Fz and My movement, the need for a relatively thick and rigid waveguide is obviated. This allows freedom to use any number of designs. The simplest beam cross section is a rectangular flat beam. The beam material may include stainless steel, titanium, aluminum, layered graphene, and even Pyrex or industrial diamonds. The choice is based on the efficiency of transmitting sound energy, the speed of sound through the beam material, the stiffness of the material, and the need to bend the beam for specific anatomic access.

The efficiency of transmission is important so as not to lose sound energy as the sound travels from proximal end to distal effector end. Certain crystalline structures tend to dissipate the sound or redirect it. Stainless steel and titanium are excellent for transmission.

High-speed transmission of the sound energy within the waveguide results in a high angle of internal reflection as the sound moves through the material. This is important for the situation calling for a bend in the cantilevered beam such as for ergonomic purposes and for placing the distal tip in an optimal position relative to the surgical site. If the angle of internal reflection is too small, the energy will prematurely exit the beam.

The shape of the beam is wide at the proximal end to accommodate the MFCs and the blocking mass. The beam then rapidly tapers toward the distal end or tip. The more the beam narrows, the higher the energy concentration at the tip. The shape of the taper varies. In a preferred embodiment the curve is a Bezier. Other curves have advantages as well including a catenary and an exponential or a logarithmic curve. Straight tapers and stepped beams are not as efficient. The distal tip can be thinned between the two flat sides near the tip. The thickness of the beam is based on the stiffness of the beam material and the amount of whipping action desired. If the beam is too thin, the whipping is slow and weak. Too stiff and it only produces limited movement.

Other cross-sectional beam shapes are possible. A circular shape or rod will have less bias on tip movement. This, in combination with Fz and My movement, can trace many paths that can be used for more rapid tissue destruction. Ribs on the side of a rod beam can direct the movement. Also the combination of Fz and My movement will increase the area of the tissue destruction reducing the time it takes to do the surgery.

The distal tip can be one of many shapes. For movement in the Fz mode (along the longitudinal axis of the beam), the larger the area of the beam's end, the more negative pressure imparted to the liquid and the better quality of cavitation. A flared flat end presents more area to the target tissue. If a flat end is tilted it will enter tissue better. The more surface area in the tissue, the more tissue that is simultaneously removed. Thus, inserting the flared flat end into the tissue produces cavitation on both of its sides. Another embodiment would have a series of these tilted flat surfaces with a sharp tip, essentially creating a screw shape for easy insertion into the tissue and thus causing a long region of tissue disintegration.

As the flat beam has a transverse (My) movement in one direction only, a twist in the beam end can turn the tip 90 degrees and present the tip movement along a different axis. If this edge is sharpened it becomes a knife-edge and makes this My movement applicable to incising. Other shapes are useful. A saw tooth can be used to cut bone, a rasp can abrade bone, and other tips are useful for dissecting through tissue, causing subsurface disintegration, elevating tissue off of bone, and causing coagulation. Those familiar with the art can devise other shapes.

The actual surface of the beam tip is important to ways of increasing efficiency of the tissue effect. Thus, a claw end or a file end can be used for tearing tissue and for wearing down bone. This is more important in the My movements.

Where cavitation is important a space between parts of the tip produces increased effect. A simple example is the open slotted end. This can be modified as a closed slot or a circular or hoop shape.

The MFC can be made as a cylinder with a spiral piezo composite. This will produce a twisting action in the beam. Placed on the proximal end of a cantilevered rod the tip movement can attain an $M_y$ mode that is chaotic. Specially designed outer ribs on the rod or conversely slots along the rod can create various patterns of movement.

More advanced beams use multiples of these basic, simple flat beams or can be of a hollow rod shape. Using the walls of a hollow rod or tubular shape is very efficient in carrying sound energy. The end of a tube beam can have multiple slots and thus produce a series of tabs or fingers that act each in its own My plane causing very effective tissue reduction. The effect is to increase the amount of energy brought to the target tissue. More energy results in faster tissue removal. Also, these arrangements can house suction and irrigation ports as well as a port for an endoscope within the tube, an advantage in freeing a hand of the surgeon.

Of importance is the blocking mass at the proximal end of the beam. This is both the clamp for the cantilever and for preventing sound energy from traveling proximately toward the surgeon. The block is made of high elastic modulus material (for example steel or tungsten) and as such does not absorb much energy and actually reflects it back in a distal direction. The blocking mass has a very high density and reflects the sound waves efficiently. The distance between the blocking mass and the MFCs is critical to efficient transfer of as much energy possible in a distal direction. The ideal distance is such that the waves reflected off of the blocking mass are in phase with the waves from the MFCs going towards the distal end of the beam and do not destructively interfere.

One advantage of the MFCs is their rapid response to changes in current flow with relatively large elongation and contraction. In addition, the lack of hysteresis results in high response rates up to about 100 kHz.

Another advantage is the flat configuration and the ductility of the MFC pad. This makes design of the beam easier while still preserving the ability to visualize the target tissue deep in a passage and yet have an ergonomically comfortable tool.

The MFCs are preferably attached to the beam with high shear strength epoxies that can withstand the large forces at play. The relation of the pads relative to each other are in a lengthwise or in a lateral orientation. Thus, MFC pads can be applied to the beam side to side with each other or end to end along the longitudinal axis. The proximal end can be lengthened or widened to accommodate more MFCs. A widened flat beam can be bent for ergonomic reasons and still have high energy levels delivered. MFCs can be cemented on opposing surfaces and interact with other additional MFCs. MFCs can be stacked on each other, though from a practical standpoint a stack of three is the maximum used. The first stacked MFC adds only another 50% of the power of the MFC attached to the beam and the second stacked MFC only adds an extra 25%. Using these manipulations, a large number of MFCs can be activated in unison for the delivery of a powerful end force.

The simultaneous stimulation of all the MFCs in synchronism will produce substantial longitudinal (axial) reciprocation and power. This is needed for cavitation. In contradistinction, if the MFCs are made to actuate in a temporally staggered manner across the beam with the signals to the MFCs on one side producing elongation when the fibers on the opposed side produce contraction, the result is a transverse wave and a subsequent whipping action. This transverse wave may produce a standing wave that approximates the natural frequency of the beam waveguide.

MFCs can also act as sensors. A tiny MFC attached to the beam can generate signals that vary with the distal end motion. As the beam encounters different tissues with differing viscosities or stiffness, the amplitude of the signals change. This is sensed through a feedback circuit and the frequency in the beam can be adjusted. At the same time, the changes in amplitude can be used to alert the surgeon. The current drawn by the device can also be used to monitor resistance and dampening by the beam due to different densities of the material. In an example situation, with a rapid dampening or a change in the stiffness or viscosity of the tissue may indicate that the beam is nearing bony attachment. Sudden increase in amplitude indicates the beam has exited the tissue and is sitting in air. Detection of either of these events is of importance to the safety of surgery.

Key to this invention is the ability to intermingle two movements at the distal end of the beam. These two movements are produced by the interaction of the MFCs on the proximal end. In its simplest form an MFC is applied on either side of the proximal portion of the flat beam. If the electrical potential is applied at the exact same time to each and they are poled to move in the same direction, an extensional mechanical or sound wave is sent down the beam. This is the Fz movement. If, however, the stimulation of the two sides are out of phase by 180 degrees, one MFC will be lengthening and the other will be contracting. This will cause a bending of the beam at the midpoint of the two MFCs and is equivalent of a transverse force applied at right angles to the flat side of the beam. This is the My movement.

To make this rapid change the electronic control of the electrical power is key. In one preferred embodiment an H-bridge is used to rapidly switch the excitement of the two MFCs. In this preferred embodiment the electrical signal can be turned on and off very rapidly. Thus, very short bursts of high frequency waveforms to create Fz and then low frequency waveforms to create My movement can be intermingled. The bursts and intervals are so short that it appears as if both are operating at all times. Yet the activity of each is different. Fz is producing the kind of motion that produces cavitation for tissue destruction by cavitation as well as exciting local coagulation. The My is producing a much slower movement that whips the tip to tear or incise the tissue. The result is disintegration of the tissue or clean incisions depending on the tip used. For different purposes the amount of time in each mode can be varied. Overall there is disintegration or incision or dissection or coagulation or other treatment effects created at the distal end of the beam.

In the brief intervals between these two modes a fast sensor can look for dampening of the tip motion. A feedback to the microprocessor which controls the signal generator can compensate for the dampening. Again the feedback is continuous so seamless monitoring and control is achieved.

The electrical power for this device in one preferred embodiment is a DC current provided by a battery, however a medical grade isolation transformer and power supply will also work. This current is controlled by a MOSFET to produce a square wave signal in the primary of a transformer. The voltage is stepped up in the secondary to hundreds of volts. The square wave leaving the secondary passes through a capacitor and a diode forming a clamping circuit. A sine or triangular wave is formed and drives the MFC such that they are forward biased in the Fz mode. This is important as the MFCs typically can be driven to +1,500 volts in the forward biased mode, but only 500 volts in the reversed biased mode. Important for this device is the low voltage (battery) source for the transformer. Besides making the device more transportable it is safer than a conventional wall source and obviates concerns of a ground fault and possible electrocution of the patient or surgeon.

BRIEF DESCRIPTION OF THE DRAWINGS

Other objectives, advantages, and applications of the present invention will be made in the following detailed description of preferred embodiments of the invention. The description makes reference to the accompanying drawings in which:

FIG. 4 is a side view of a cantilevered beam employing two parallel beam sections at its distal end and having MFCs adhered to both outer sides of the two beams and having its proximal end anchored in a relatively massive sound blocking clamp;

FIG. 5A is a plan, partially broken away, view of a tubular cantilevered beam;

FIG. 5B is a cross section taken along line A-A of FIG. 5A;

FIG. 5C is a cross section taken along line B-B of FIG. 5A;

FIG. 5D is a cross section taken along line C-C of FIG. 5A;

FIG. 5E is a cross section taken along line D-D of FIG. 5A;

DETAILED DESCRIPTION OF PREFERRED EMBODIMENTS OF THE PRESENT INVENTION

The present invention broadly employs a cantilevered beam, relatively rigidly supported at the proximal end and free to oscillate at the distal end, supporting MFCs on its surface which are electrically powered to induce a variety of motions of the distal end of the beam. A first preferred embodiment of the beam is illustrated in FIGS. 1A-1D.

The beam itself, indicated at 10 in FIGS. 1A-1D, is formed as a thin, generally flat beam formed of a sheet material, preferably stainless steel, but which could include other materials, in particular metals, which are relatively rigid such as titanium, aluminum, or materials such as graphene, Pyrex glass, or industrial diamonds. The beam 10 preferably has a relatively uniform thickness along its length, which may be in the range of 0.0040 to 0.0070 inch.

Figure 1:
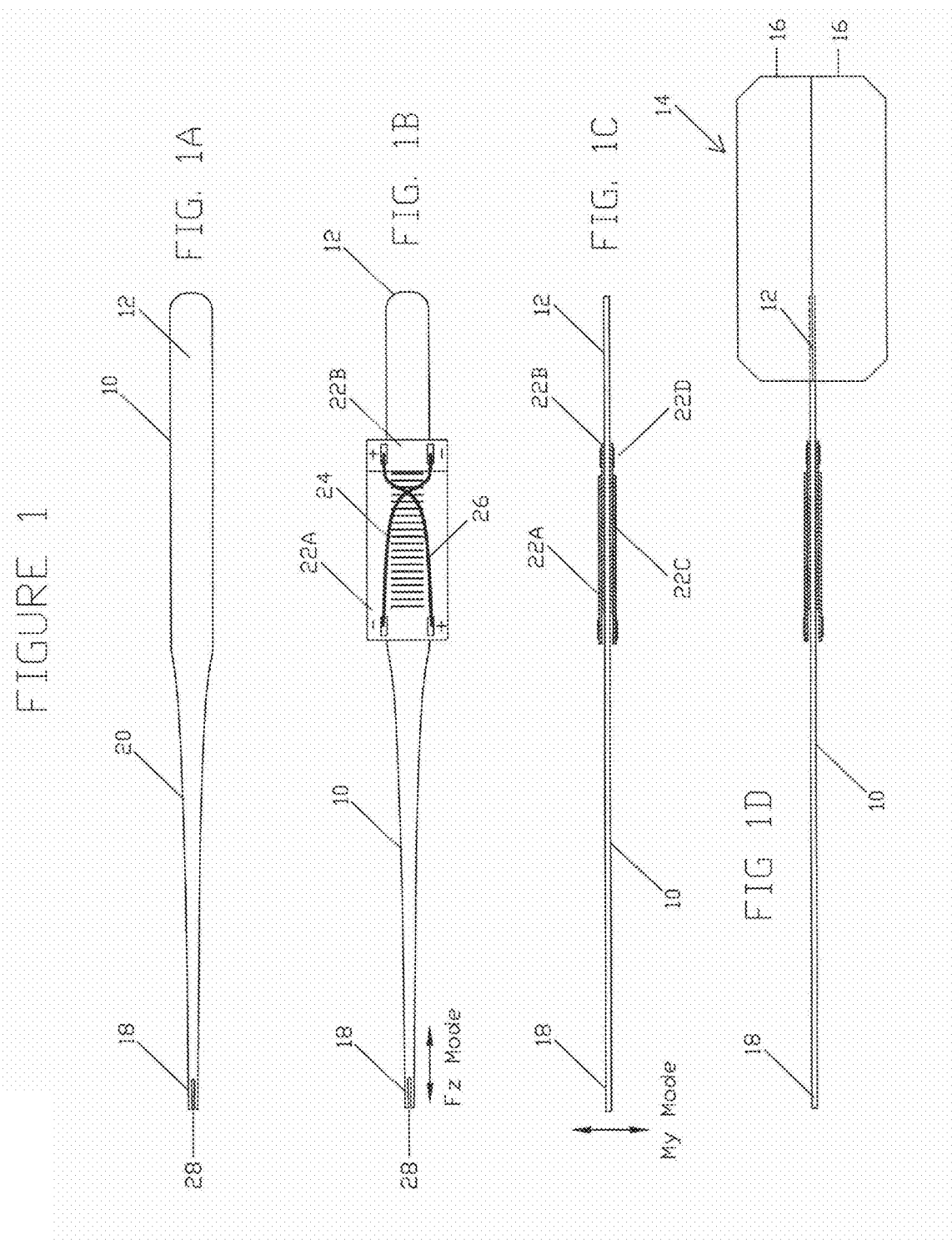
FIG. 1A is a plan view of a cantilevered beam used in a preferred embodiment of the invention and having a slotted tip.
FIG. 1B illustrates the cantilevered beam of FIG. 1A with macro fiber composites (MFCs) adhered to one of its surfaces, with two MFCs connected in parallel.
FIG. 1C is a side view of the cantilevered beam of FIG. 1B.
FIG. 1D is a side view of a cantilevered beam, like FIG. 1C, with its distal end embedded in a sound blocking clamp.

The relatively wide end of the beam, referred to as the proximal end 12, is relatively rigidly supported in a blocking mass generally indicated at 14 in FIG. 1D and consisting of a pair of metal blocks 16 which have mating flat surfaces that clamp the proximal end 12 of the beam 10. The clamp may be formed of a dense metal, such as tungsten, to better reflect proximal directed vibrations from the MFCs. The free end of the beam extending beyond the clamp 14 may typically be 7 inches in length or multiples of the half wave length, all dependent on the frequency used. The proximal end 12 of the beam 10 may have a width in the range of 0.4 to 1 inch in width while the distal end 18 of the beam may typically have a width of 0.8 inch. Other dimensions are possible. The relatively wide proximal end of the beam 12 and the distal end of the beam 18 are connected by a curved and tapered section 20. As has been noted, the preferred embodiment of the taper is a Bezier curve. Other curves such as a catenary, an exponential, or a logarithmic curve may be employed as well as a straight taper and a stepped beam. The beam may be thinned toward the distal end 18.

The MFCs are typically flat and rectangular, and as illustrated in FIGS. 1B-1D may be applied to both flat sides of the beam 10 at a slightly separated distance from the blocking mass 16. As disclosed in FIG. 10, subsequently described in detail, each MFC consists of rectangular rows of piezo crystals embedded in a fibrous composite and shaped into rods. These are sandwiched between layers of adhesive, electrodes, and a protective film. The electrodes are attached to the film in an interdigitated pattern which transfers the applied voltage directly to and from the ribbon-shaped rods. The MFCs are available from Smart Material Company, Sarasota, Fla., and are described in U.S. Pat. No. 6,629,341, the disclosure of which is incorporated herein by reference. These MFCs may be applied to structures so as to bend or distort the structures, counteract vibrations, or generate vibrations. The materials also act as a very sensitive strain gauge, sensing deformations, noise, and vibration, making them useful for the feedback applications of the present invention.

In order to control the MFCs, a microcomputer will be used. It may be an embedded computer or an external computer.

The computer will control the frequency, amplitude and phase of the MFCs and may have a user interface that can contain buttons, potentiometers, and a display (not shown). This computer will also have sensor inputs to monitor the beam while in use. One sensor can be a section of an MFC epoxied on the beam that will generate a voltage proportional to the beam's vibrations. Yet another sensor will be a current sense of the generator power. In practice, the current draw will increase when the beam distal end encounters material such as tissue and bone. The current draw is minimum when the beam is subjected to air.

The MFC or other piezo sensor voltage will be maximum at the beam resonance frequency, and will decrease when the beam is pulled off resonance by encountering tissue or bone. Normally the microcomputer code will change frequency to obtain resonance again, however if it determines that bone has been touched, then it will shut down the generator and alert the surgeon. There may be cases where bone must be destroyed as well, and this would be a user input to the computer so that it would not shut down the generator, and would optimize the frequency, amplitude, and phasing of the MFCs to achieve the desired result.

The embedded microcomputer can be connected to a PC or other computer such as a tablet. This will provide for data recording, graphing, and sending new code to the embedded microcomputer so that it will be optimized for the particular operation.

Time stamping of the data will occur at the embedded micro and will be sent along with the data.

Additionally, an endo scope camera (not shown) can be connected to the PC or other computer so that the data from the embedded micro can be time synchronized with the camera data for post processing, statistical analysis, and teaching other doctors, medical students and others in the medical field.

The connection from the embedded micro to the line powered PC will be done so that no common grounds are shared. This is used to prevent ground faults from the line power computer to be transferred to the patient or surgeon. This can be accomplished by wireless transmission, or an optically isolated link such as an OPTO USB connection.

In FIGS. 1B and 1C two layers of MFCs are applied to each side of the beam 10. MFCs 22a and 22b are applied to the top side, with the units largely overlapping and only the underside units' electrical contacts being exposed. As shown in FIG. 1B, these contacts are preferably connected in parallel by wires 24 and 26. The two bottom layers 22c and 22d are similarly disposed and configured and may be connected in parallel to the upper units 22a and 22b to provide larger deformations.

Figure 7:
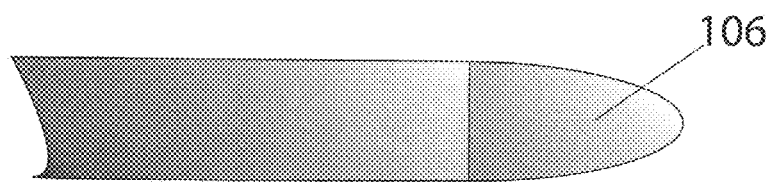
FIGS. 7A-7H and 7J-7T illustrate a range of cantilevered beams having different tips for use in various surgical situations.
Figure 7:
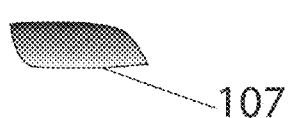
Figure 7:
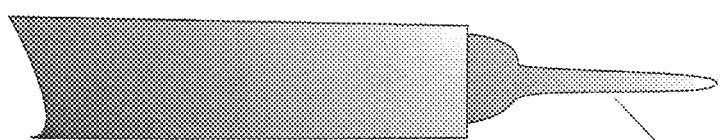
Figure 7:
Figure 7:
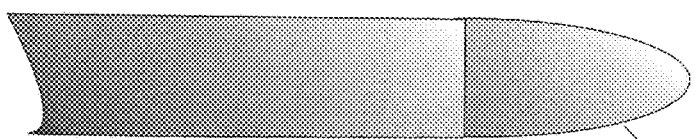
Figure 7:
Figure 7:
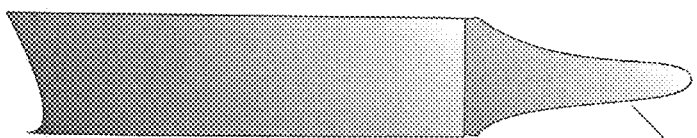
Figure 7:

The beam 10 has a slot 28 at its distal tip for purposes of enabling various surgical operations. A variety of other tip designs, some of which are illustrated in FIG. 7, may be employed.

Figure 2:
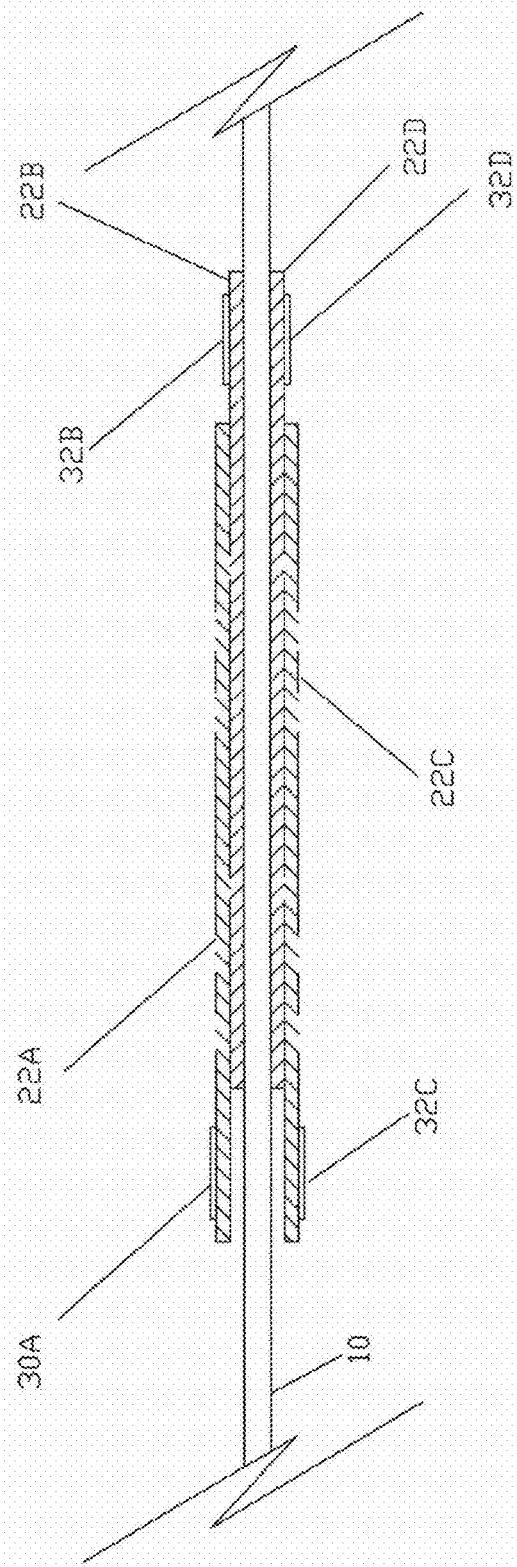
FIG. 2 is an enlarged side view of the section of the cantilevered beam having MFCs applied to its two opposed surfaces.

FIG. 2 is an enlarged side view of the section of the beam 10 incorporating the MFCs. FIG. 2 illustrates the electrical contacts 30a and 30b for the two upper MFCs and 32c and 32d for the lower MFCs. The MFCs are powered by battery powered AC generators illustrated in FIG. 9.

Figure 3:
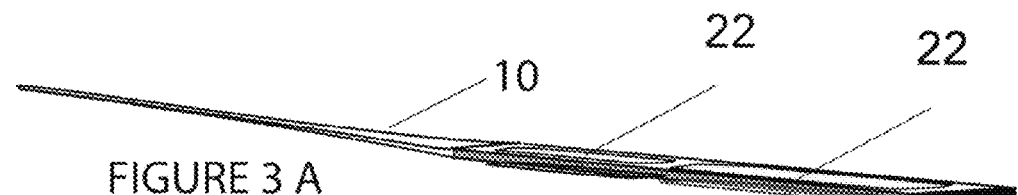
FIG. 3A is a perspective view of the cantilevered beam of FIGS. 1A-1D, having a straight distal end.
FIG. 3B is a perspective view of a cantilevered beam having a downwardly curved distal end.
FIG. 3C is a view of a cantilevered beam having a straight distal end with a proximal end widened to accommodate additional MFCs.
FIG. 3D is a perspective view of a triangular beam supporting multiple MFCs at its proximal end and having a channel that can carry suction, irrigation, and other devices to augment tissue ultrasound interactions.
Figure 3:
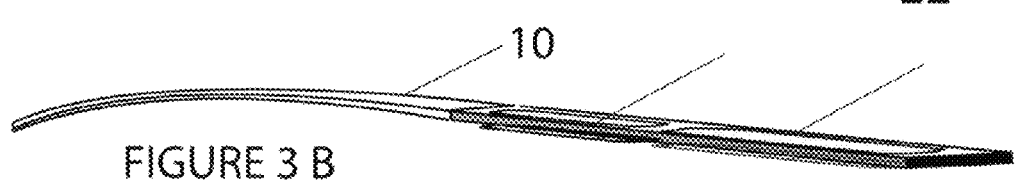
Figure 3:
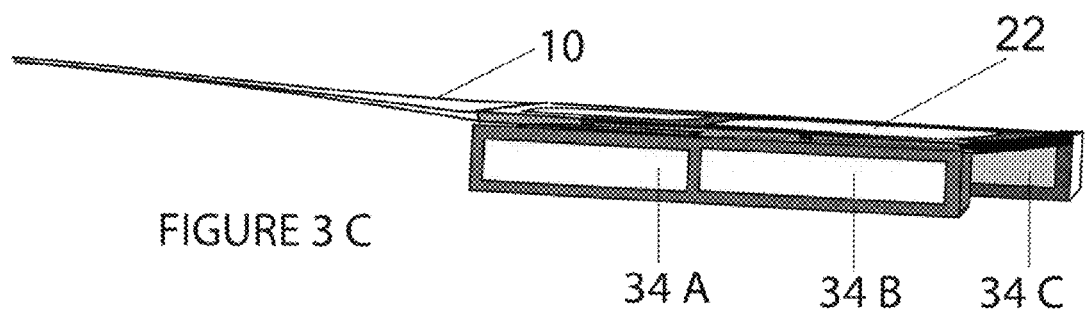
Figure 3:
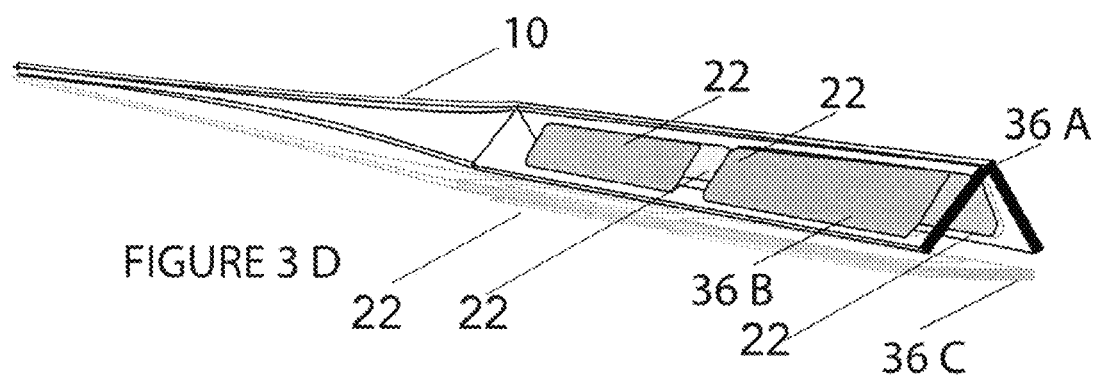

FIGS. 3A, 3B, 3C, and 3D are perspective views of various beam configurations for the cantilevered beams of the present invention showing their supported MFCs 22, but not the blocking masses 14. FIG. 3A illustrates a straight beam, much like illustrated in FIGS. 1A-1D; FIG. 3B illustrates a beam curved along its length; FIG. 3C illustrates a beam having panels which extend normally to the MFC units 22 to support additional MFCs 34a and 34b on one side and 34c on the opposed side. FIG. 3D illustrates a beam having three sections, 36a, 36b, and 36c joined together at their edges in a triangular configuration enclosing a central space that can carry various ports (not shown) for purposes like suction, irrigation, endoscopy, and other surgical purposes. The outer sides of the sections 36a and 36b can carry MFC units 38, which can intensify the motions induced by the MFCs 22.

The dual layer beam 40, 42 illustrated in FIG. 4 has two overlying MFCs 44 and 46 on one of its outer sides and MFCs 48 and 50 on the other outer side. The proximal ends of the beams 40 and 42 are supported in a relatively massive sound blocking clamp 52 comprising a pair of elements 54 and 56 each having flat, mating surfaces. The proximal ends of the two beams 40 and 42 are embedded in an opening in the blocks 54 and 56 and separated by a spacer 58. The blocks 54 and 56 are adapted to accommodate screws (not shown) which pass through the block 54 and thread in the block 56.

This configuration can provide strong energy delivery to the distal ends of the beams 40 and 42. The distance from the MFCs to the clamp 52 is preferably an integral number of wavelengths to ensure that the vibrations passing in the proximal direction from the MFCs will be reflected by the clamp, back to the MFCs, so that they reinforce, rather than cancel, the basic vibrations made by the MFCs.

FIG. 5A discloses an embodiment of the invention employing a tubular cantilevered beam generally indicated at 60. This embodiment has the ability to accommodate a plurality of MFCs 62 which are illustrated in the cross section of FIG. 5D. A total of eight MFCs are employed with four of them, denoted 64, being spaced about the outer side of the beam and an additional four, denoted 66, are accommodated on the interior of the beam. These can be stacked with a theoretical 24 MFCs acting on the beam. This provides a high energy output at the distal end of the beam 60. The interior of the beam can accommodate one or more ports 68 which can carry irrigating fluid and provide suction removal for the destroyed tissue and any irrigating fluid. It could also carry a rigid or flexible fiber optic endoscope for surgical viewing. The tube 60 may gradually converge into a square shape 68 in a proximal direction, so that the proximal end 70, illustrated in cross section in FIG. 5E, is fully rectangular. This rectangular proximal end can accommodate a number of blocking masses 72 on its four sides which increase the overall mass of the proximal end of the tube. Screws 74 join the masses to the proximal end.

The separation of the MFCs 64 from the blocking mass 72 is designated 19 in FIG. 5A.

Figure 6:
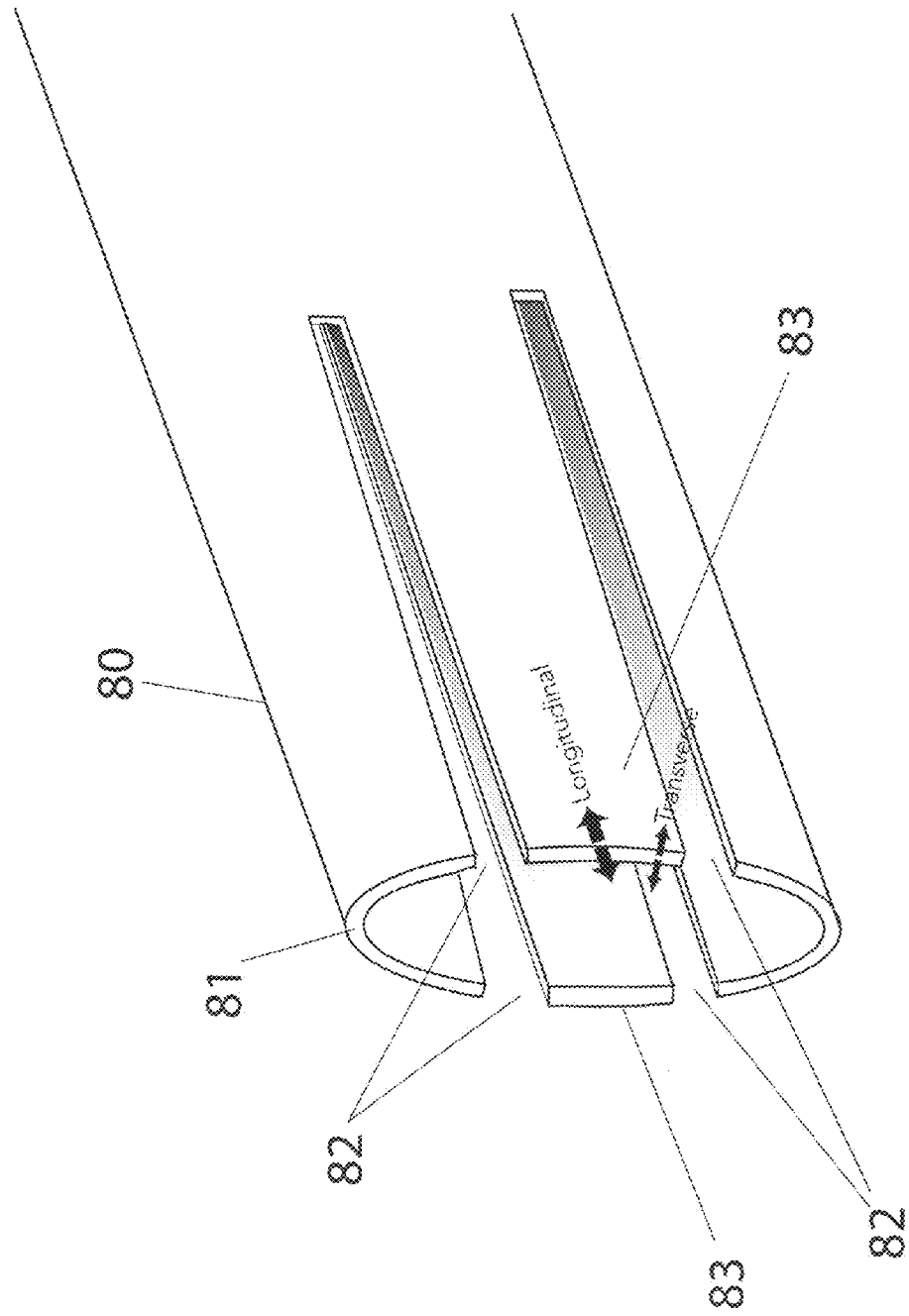
FIG. 6 is a detail of the distal end of a hollow beam tip with slotted ends.

In another variation of the invention a tubular beam tip, illustrated in FIG. 6 as 80, may have a number of slots 82 creating "fingers" extending from its distal end to allow for increased whipping action of the distal end and transfer of energy into the tissue to be treated.

The distal tips of the beam may take any of a variety of forms useful to the surgeon to perform particular operations. FIGS. 7A-7H and 7J-7T disclose a variety of tip forms. FIG. 7A shows the distal end of a cantilevered beam 90 having a flat, plain end.

FIG. 7B illustrates a beam end having a flat end expanded laterally at 84 to form a circular end.

FIG. 7C shows a similar flat end 86 which is angled with respect to the central axis of the distal end of the beam. This allows easier entry into tissue so the entire flat plane can be inserted.

FIG. 7D shows a distal end taking the form of a screw 88. Multiple flat plates as in 7C are arranged on the distal end of the rod beam with a sharp screw point to start the end piece into the tissue. Thus all plates may generate cavitation and movement.

FIG. 7E is a distal end with a flat end extended laterally and a concave flare 92 at the immediate distal end adjacent to the end 90.

FIG. 7F shows a plain flat rectangular distal end for the beam.

FIG. 7G illustrates a beam end with a slot parallel to the axis of the beam immediately adjacent the end of the beam, with the slot closed off by the beam.

FIG. 7H is an illustration of a beam end with an open slot 98. The width of the slot can vary as well as the shape of the sides of the slot FIG. 7J is an illustration of a beam end with a rounded edge 100. This can also be a sharp edge.

FIG. 7K is a perspective view of a beam end with a looped slot 102.

FIG. 7L shows a beam with a distal end 104 which is decreased in thickness relative to the proximal balance of the beam.

FIG. 7M is a plan view of a beam end with a dissector tip 106.

FIG. 7N is a side view of the tip 106.

FIG. 7O is a plan view of a beam with a disintegrator tip 108.

FIG. 7P is an end view of the tip 108.

FIG. 7Q is a plan view of a distal tip end 110 which is elevated out of the plane of the balance of the beam as illustrated in FIG. 7R. This tip is useful for elevating soft tissue off of a bony surface.

FIG. 7S is a plan view of a beam with a coagulation tip 112 which has a tapered pointed end 114 as illustrated in FIG. 7T.

Figure 8:
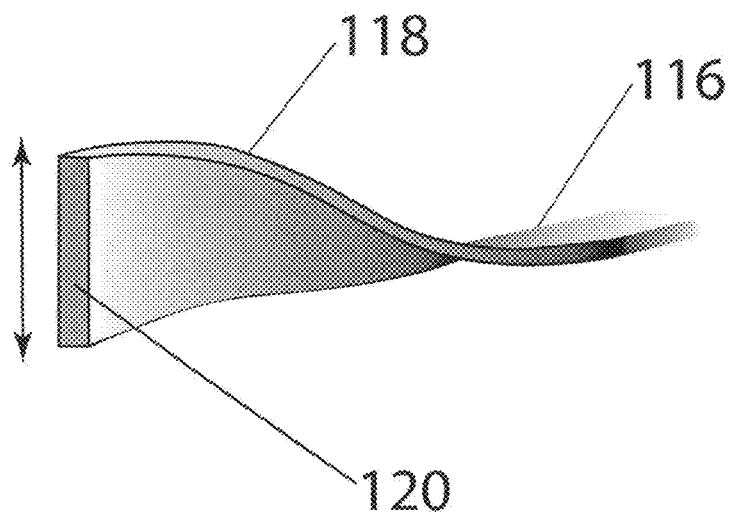
FIG. 8 is a perspective view of the distal end of a cantilevered beam for use with the present invention having a 90 degree twist at its distal end to convert an My movement into a cutting movement.

FIG. 8 illustrates a distal end for a beam 116 with the distal end 118 twisted by 90 degrees out of the plane of the proximal portion of the beam and ending with a sharpened cutting end 120 for cutting soft tissue. This could alternatively be a saw-tooth type end or the like for providing bone cutting motion based on actuation of the MFCs to produce My movement. This end could also end as a rasp for thinning or removing thin layers of bone.

Figure 9:
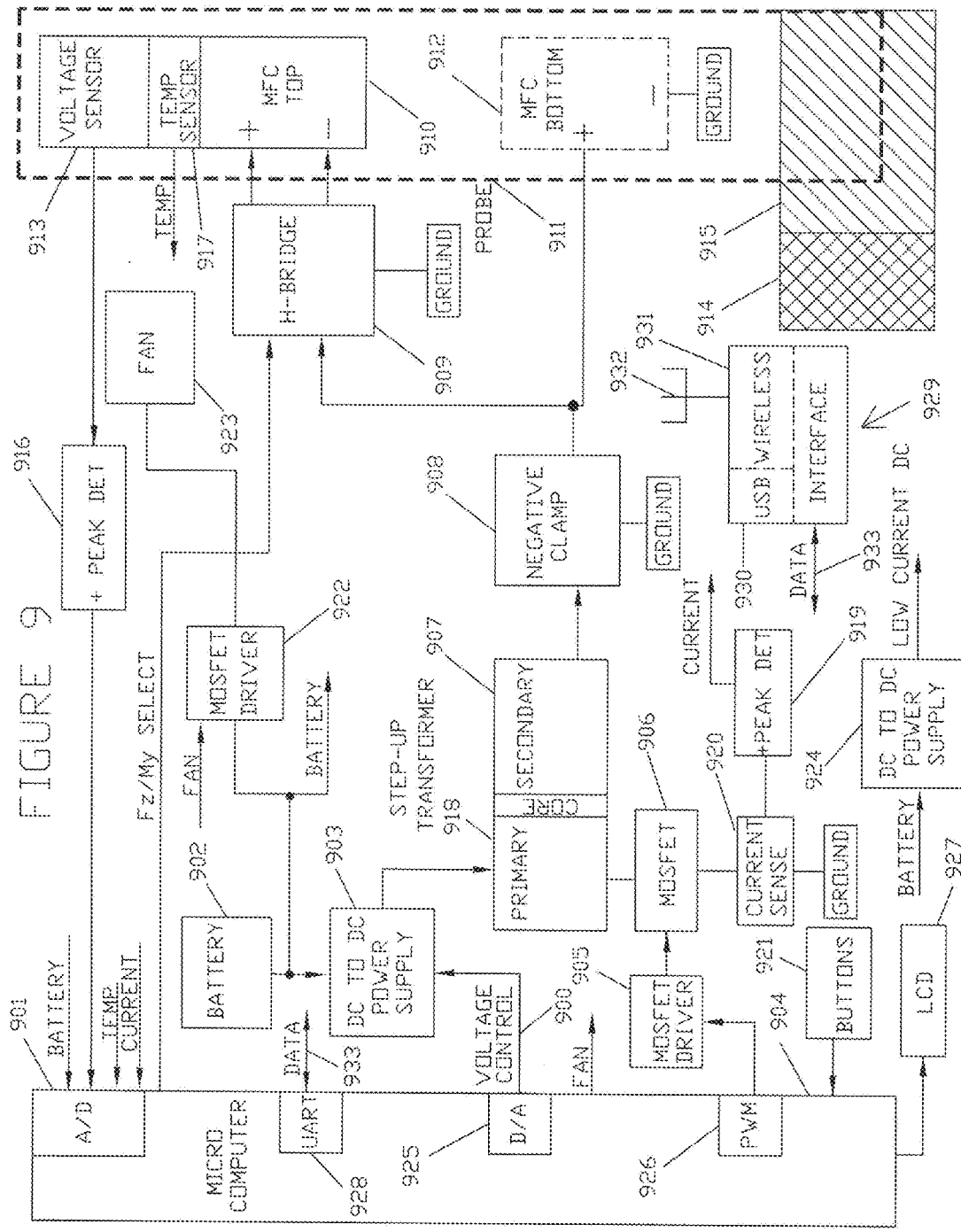
FIG. 9 is a block diagram of a computer controlled system for generating AC driving waves for the MFCs employed with the present invention and for detecting the beam's tip displacement for feedback purposes to control the generated signals.

The control signal generator and feedback circuit for the beam 10 is illustrated in the block diagram of FIG. 9. Broadly, the circuit operates upon a DC supply to generate an alternating current signal approximating a sinewave or triangular wave or saw-tooth wave to power two MFCs disposed on opposite sides of a cantilevered beam, designated the top MFC 910 and the bottom MFC 912 disposed in a beam 911, as illustrated in FIG. 9. The circuit also uses an MFC as a signal generator 913 to detect the deflection of the tip of the beam 911 and feed that signal back through a peak detector 916 to the circuit which generates the AC signal for the two MFCs.

The power for this device is a battery 902 or some other source of DC power that can produce a DC voltage for operation on by microcomputer 904. The microcomputer 904 employs an analog to digital converter 901 which generates a DC voltage control signal on line 900. The signal is provided to a DC to DC power supply 903. The voltage from this power supply is then applied to the primary 918 of a step-up transformer forming part of what is termed a "sinewave generator" although the signal may be more like a triangular wave or saw-tooth wave. The sinewave generator is composed of the microcomputer 904; the battery 902; the DC to DC power supply 903; the step-up transformer 918, 907; a negative clamp 908; a MOSFET driver 905; a MOSFET 906; and an H-bridge 909.

With the beam tip exposed to free air, the microcomputer programming will maximize the output of a voltage sensor 913 which measures the displacement of the tip of the beam 911. The sensor 913 can be formed by an MFC which produces a voltage when movement is encountered. The positive peak detector 916 produces an AC voltage that corresponds to the peaks of the tip motion sensed by the voltage sensor 913 and produces a voltage proportional to the displacement of the beam tip. Under control of the signal from the peak detector 916, the microcomputer 904 produces a square wave that is connected to the MOSFET driver 905 which increases both the voltage and current to drive a MOSFET gate 906 which has a large capacitance and therefore requires a driver that can supply the necessary current.

The MOSFET 906 has its source connected to ground so that when it is turned on the drain will go close to ground and supply a voltage differential to the primary 918 of the step-up transformer as a result of the other side of the primary winding being connected to the DC to DC power supply 903.

The secondary 907 of the step-up transformer is connected to the negative clamp circuit 908 that keeps the secondary voltage at a positive value. This is desirable because the MFCs can be driven to a positive 1500 volts if they are forward biased and only 500 volts if they are negatively biased. Because the load on the secondary of the transformer 907 is primarily capacitive, like the MFCs, the secondary of the transformer in the capacitive load creates an electrical tank circuit.

When the beam is exposed to tissue it may be pulled off of its resonant frequency in free air and the program of the microprocessor 904 will adjust the frequency of the sinewave generator to maximize the voltage displacement detected by the sensor 913. If, however, a sudden drop of voltage is measured by the A/D 901 from the positive peak detector 916, the program running in the microcomputer will shut down the DC to DC power supply and signal the surgeon that the beam may have contacted a hard substance such as bone. When the beam is in tissue, the output from the sensor is reduced from its voltage in free air.

The power to the beam MFCs is controlled by the microcomputer 904 using a digital to analog converter 925 which provides output on line 900 to the DC to DC power supply 203. The power can be adjusted by the surgeon using up/down buttons 921 providing input to the microcomputer 904.

The beam MFCs can be operated in phase such that the distal end of the beam moves in and out along the central axis of the beam or may be operated out of phase such that the distal end of the beam is forced to move perpendicular to the wide axis of the beam. The phase of the two signals is controlled by the microcomputer 904 through an H-bridge 909. The H-bridge switches the leads of one of the MFCs so it either expands at the same time as the opposite MFC to produce Fz motion or so they expand out of phase producing an My motion so that the MFCs cause a whipping action of the beam tip to occur. The H-bridge 909 is controlled by the Fz/My select signal, an I/O bit of the microcomputer 904.

The current of the sinewave generator is measured by the microcomputer A/D circuit using a current resistor 920 in the grounding circuit of the MOSFET 906. The current envelope signal from the peak detector 916 is measured by the A/D circuit of the microcomputer. This current will change with various beam loading and can be used to optimize the tissue destruction, or cut off power to the beam tip if the program instructs it to do so. The voltage displacement sensor 913 may be an MFC or other piezo device, strain gauge, an electromagnetic device, or any other type of small displacement sensor. If the MFC is used, it produces a voltage using the piezoelectric effect. A + peak detector 916 is used to convert the AC voltage into a + voltage envelope that the A/D can easily convert to a digital value.

The microcomputer 904 controls a MOSFET driver 922 which controls a fan 923 that cools the MFCs 910, 912 and also controls the waste heat from a Peltier junction 914 which cools the blocker 915 which supports the proximal end of the beam 911. The blocker 915 is made of a high modulus of elasticity material so that it reflects rather than absorbs the waves emanating from the MFCs toward the proximal end of the beam 911 back toward the distal end, rather than absorbing those waves. The distance from the end of the blocker to the MFC must be adjusted so that the reflected waves from the blocker are in phase with the MFC waves going toward the distal end of the beam, or energy will be lost.

Figure 10:
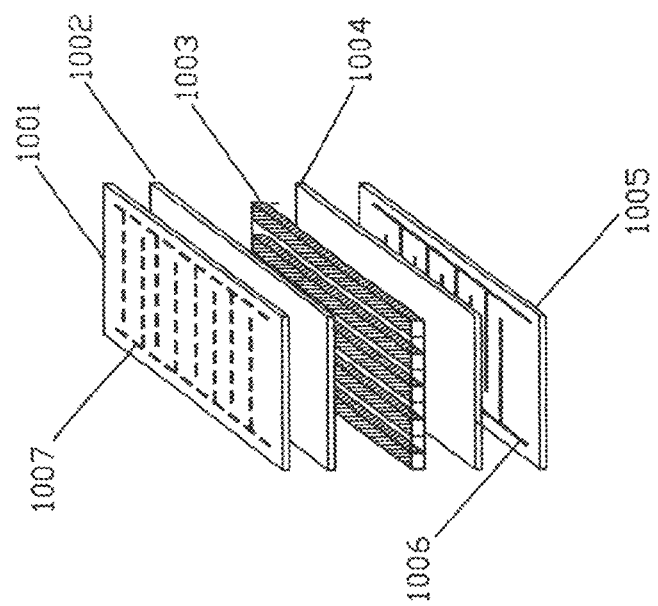
FIG. 10 is a diagram of a preferred version of the MFCs.

A typical macro fiber composite (MFC) useful in the present invention is illustrated in FIG. 10 in exploded form before joining layers into a single composite structure. The top layer 1001 is formed on a rectangular layer of polyimide film and constitutes a pair of electrode structures 1007 consisting of two side electrodes (shown in phantom as they are formed on the underside of 1001), which are connected to the two output terminals of the H-bridge 909. Each of these side electrodes has a group of electrode fingers extending normally to the side electrodes toward the opposite electrodes. These finger electrodes do not contact one another but are intended to bear against the epoxy structure so as to apply their opposite polarity electrical current to the piezo ceramic rods 1003.

The second layer 1002 is a structural epoxy and supports and bonds the other actuator components together.

Layer 103 is a sheet of aligned rectangular piezo fibers embedded in a fiber composite material. These constitute composite rods with piezo fibers integrated in them. The fourth layer 1004 is another layer of structural epoxy like layer 102. The fifth layer 1005 is another interdigitated pattern of electrodes like the top layer 1001. When the layers are joined by the epoxy sheets they form a thin surface-conformable sheet in a sealed and durable ready to use package. The electrodes are attached to the film and contact the ribbon-shaped rods of layer 1003 to transfer the applied voltage directly to and from the ribbon-shaped rods. When the assembled unit is affixed to one of the beam beams such as 10, the electrical actuation of the ceramic rods of layer 103 can cause expansion or contraction of the surface of the beam to which they are attached. It can also act as a generator, sensing motion of the beam tip 18 for feedback purposes as has been noted.

Having thus described our invention, we claim:

1. A system employing an elongated cantilevered beam having proximal and distal ends, with the distal end adapted to be inserted into a body passage so that it engages target tissues to produce therapeutic effects on the tissues, comprising:
   piezoelectric material fixed to a surface of the beam adjacent to the proximal end of the beam;
   an electrical excitation system connected to the piezoelectric material, adapted to apply reciprocating currents to the material to produce deformations of the beam;
   a piezoelectric sensor for detecting an amplitude of deformation of the beam, and wherein the sensor is connected to said excitation system to determine degree of engagement of the beam with the target tissues and to modify the excitation of the piezoelectric material to control the engagement of the beam with the target tissues; and
   further comprising a blocking mass from which the beam is cantilevered, wherein the blocking mass is made of high elastic modulus material and is disposed to reflect energy back towards the distal end of the beam and prevent energy from spreading to the proximal end of the beam.

2. The system of 1 wherein the piezoelectric material is fixed to two opposed surfaces of the beam.

3. The system of claim 2 wherein the electrical excitation system for the piezoelectric material has an output; and the system further comprises electrodes connected to the output of the electrical excitation system, said electrodes having an interleaved pattern, so as to apply alternating current to the piezoelectric material.

4. The system of claim 1 wherein the piezoelectric material is in the form of macro fiber composites.

5. The system of claim 1 wherein the piezoelectric material comprises piezoelectric fibers that are formed as macro fiber composites.

6. The system of claim 2 wherein the electrical excitation system is connected to the piezoelectric material fixed to the two opposed surfaces of the beam by a switching circuit capable of applying power to the piezoelectric material on both surfaces in unison with zero degree phase shift to produce reciprocating axial motion of the beam or, alternatively, applying power to the material on both surfaces in a temporally offset manner so that as one side of the beam is extending the other side of the beam is contracting, causing motion of the distal end of the beam in a direction normal to the two opposed surfaces of the beam.

7. The system of claim 6 further comprising an operator control connected to the switching circuit for connecting the excitation system to the piezoelectric material fixed to the two opposed beam surfaces either in unison with zero degree phase shift or in a temporally offset manner.

8. The system of claim 6 wherein the switching circuit constitutes an H-bridge.

9. The system of claim 1 wherein the electrical excitation system controls the frequency, amplitude, duty cycle and phase of the AC voltages applied to the piezoelectric material according to a program for the microcomputer and sensor inputs.

10. The system of claim 1 wherein the electrical excitation system further comprises a user interface that comprises input and output devices for controlling the frequency, amplitude, phase, and duty cycle of the system.

11. The system of claim 1, wherein the beam is tubular and has longitudinally extending slots opening on the distal end of the beam spaced about the circumference of the beam.

12. The system of claim 1, wherein the distance between the blocking mass and the piezoelectric material is critical such that the energy wave reflected off the blocking mass is in phase with the energy wave of the piezoelectric material.

13. A system of claim 1 wherein the beam is flat.

14. A system of claim 1 wherein the beam in width tapers towards the distal end of the beam.

15. A system of claim 1 wherein the distal end of the beam is twisted by 90 degrees out of the surface of the proximal end of the beam and is a knife-edge end for cutting.

16. A system employing an elongated cantilevered beam having proximal and distal ends, with the distal end adapted to be inserted into a body passage so that it engages target tissues to produce therapeutic effects on the tissues, comprising:
  piezoelectric material fixed to a surface of the beam between its proximal and distal ends;
  an electrical excitation system connected to the piezoelectric material adapted to apply reciprocating currents to the material to produce deformations of the beam; and
  a sensor for detecting an amplitude of deformation of the beam connected to said excitation system to determine degree of engagement of the beam with the target tissues to modify the excitation of the piezoelectric material to control the engagement of the beam with the target tissues,
  wherein the sensor for detecting the amplitude of deformation of the beam comprises fibers formed of a piezoelectric material and has an output signal which is applied to a peak detector to generate a signal proportional to the resistance to motion of the beam in response to the degree of engagement of the beam with the target tissues to regulate the excitation system.

17. A system employing an elongated cantilevered beam having proximal and distal ends, with the distal end adapted to be inserted into a body passage so that it engages target tissues to produce therapeutic effects on the tissues, comprising:
  piezoelectric material fixed to two opposed surfaces of the beam adjacent to the proximal end of the beam;
  an electrical excitation system connected to the piezoelectric material, adapted to apply reciprocating currents to the material to produce deformations of the beam, wherein the electrical excitation system has an output, and the system further comprises electrodes connected to the output of the electrical excitation system, said electrodes having an interleaved pattern, so as to apply alternating current to the piezoelectric material;
  a piezoelectric sensor for detecting an amplitude of deformation of the beam, wherein the sensor is connected to said excitation system to determine degree of engagement of the beam with the target tissues and to modify the excitation of the piezoelectric material to control the engagement of the beam with the target tissues;
  a blocking mass from which the beam is cantilevered, wherein the blocking mass is made of high elastic modulus material and is disposed to reflect energy back towards the distal end of the beam and prevent energy from spreading to the proximal end of the beam; and
  wherein the modification of the excitation of the piezoelectric material controlled by the sensor for detecting the amplitude of deformation of the beam controls the frequency of the alternating current applied to the piezoelectric material.

18. A system employing an elongated cantilevered flat beam having top and bottom surfaces and having proximal and distal ends, the beam in width being tapered towards the distal end, with the distal end adapted to be inserted into a body passage so that it engages target tissues to produce therapeutic effects on the tissues, comprising:
  piezoelectric material fixed to the top and bottom surfaces of the beam adjacent to the proximal ends of the beam;
  a blocking mass from which the beam is cantilevered, wherein the blocking mass is made of high elastic modulus material and is disposed to reflect energy back towards the distal end of the beam and prevent energy from spreading to the proximal end of the beam;
  an electrical excitation system connected to the piezoelectric material adapted to apply reciprocating currents to the materials to produce deformation of the beam in two modes,
  wherein the modes comprises a longitudinal mode to produce the deformation of the beam axial to the beam and a transverse mode to produce the deformation of the beam normal to the surface of the beam; and
  a sensor for detecting an amplitude of deformation of the beam connected to said excitation system to determine degree of engagement of the beam with the target tissues to modify the excitation of the piezoelectric materials to control the engagement of the beam with the target tissues,
  wherein the sensor for detecting the amplitude of deformation of the beam comprises fibers formed of a piezoelectric material and has an output signal which is used to generate a signal proportional to the resistance to motion of the beam in response to the degree of engagement of the beam with the target tissues to regulate the excitation system.

* * * * *